(12) United States Patent
Frenkel

(10) Patent No.: US 8,216,564 B2
(45) Date of Patent: Jul. 10, 2012

(54) COMPOSITE ONCOLYTIC HERPES VIRUS VECTORS

(75) Inventor: Niza Frenkel, Tel-Aviv (IL)

(73) Assignee: Ramot At Tel-Aviv University Ltd., Tel Aviv (IL)

( * ) Notice: Subject to any disclaimer, the term of this patent is extended or adjusted under 35 U.S.C. 154(b) by 486 days.

(21) Appl. No.: 10/476,451

(22) PCT Filed: May 2, 2002

(86) PCT No.: PCT/IL02/00345
§ 371 (c)(1),
(2), (4) Date: Oct. 31, 2003

(87) PCT Pub. No.: WO02/087625
PCT Pub. Date: Nov. 7, 2002

(65) Prior Publication Data
US 2004/0120928 A1 Jun. 24, 2004

Related U.S. Application Data

(60) Provisional application No. 60/287,717, filed on May 2, 2001.

(51) Int. Cl.
*A01N 63/00* (2006.01)
*A01N 65/00* (2009.01)
*A61K 39/00* (2006.01)
*A61K 39/245* (2006.01)
*A61K 48/00* (2006.01)
*C12N 7/00* (2006.01)
*C12N 15/00* (2006.01)
*C12N 15/86* (2006.01)

(52) U.S. Cl. ............... 424/93.2; 424/93.1; 424/199.1; 424/231.1; 435/235.1; 435/320.1; 435/457; 514/44 R

(58) Field of Classification Search .................. None
See application file for complete search history.

(56) References Cited

U.S. PATENT DOCUMENTS
5,698,431 A * 12/1997 Leib .............................. 435/236
(Continued)

FOREIGN PATENT DOCUMENTS
WO  99/07394 A1  2/1999
(Continued)

OTHER PUBLICATIONS
Verma and Weitzman, Ann. Rev. Biochem, 2005, 74:711-738.*
(Continued)

*Primary Examiner* — Robert M Kelly
*Assistant Examiner* — Kelaginamane T Hiriyanna
(74) *Attorney, Agent, or Firm* — Vorys, Sater, Seymour and Pease LLP; Susanne M. Hopkins; Ari. G. Zytcer

(57) ABSTRACT

Pharmaceutical compositions including a herpes simplex virus derived composite oncolytic vector are provided for the treatment of solid tumors in an individual. The HSV-derived composite oncolytic vector includes an HSV-derived amplicon defective viral genome carrying at least one toxic foreign gene, and an HSV-derived mutant helper virus vector that has a mutation in the vhs-1 gene. An HSV-derived mutant helper virus vector that has a mutation in the vhs-1 gene is also provided. A method for the treatment of an individual having a solid tumor is provided and includes administering an HSV-derived amplicon defective viral genome including at least one toxic foreign gene, and an HSV-derived mutant helper virus vector including a mutation in the vhs-1 gene.

11 Claims, 7 Drawing Sheets

U.S. PATENT DOCUMENTS 5,928,913 A 7/1999 Efstathiou et al.
6,379,674 B1 * 4/2002 Rabkin et al. ............. 424/199.1

FOREIGN PATENT DOCUMENTS

WO 00/08191 A2 2/2000
WO 00/65078 A1 11/2000
WO 00/77167 A2 12/2000

OTHER PUBLICATIONS

Gardlik et al., Med. Sci. Monit, 2005, 11:RA110-121.*
Markert et al, 2001, HERPES 8:17-22.*
Sena-Esteves et al., 2000, Mol. Therapy 2: 9-15.*
Everly and Read, 1999, J. Virology 73: 9117-9129.*
Goncalves, Bioessays, 2005, 27: 506-517.*
Jacobs et al., 1999, Neoplasia 1:402-416.*
Walker et al., 1998, Vaccine 16: 6-8.*
Alavi, Expert Opin biol Ther. 2001, 2: 239-52 (Abstract p. 1/1, only provided).*
Kutubuddin et al.,1999, Blood 93: 643-654.*
D, Angelica et al, 1999, Cancer Immunol Immunother 47: 265-71 (Abstract p. 1/1, only provided).*
Romi et al.,1999 J. Virol. 73: 7001-7007.*
Kirsky et al., (1998, Gene Therapy 5:1517-1530).*
Lam et al (2001, Human Mol. Genet. 10:777-788.*
Fischer et al., 1996. FASEB Journal vol. 10, pp. 126-136.*
Markert, J.M., et al., "Genetically Engineered Human Herpes Simplex Virus in the Treatment of Brain Tumours", *Herpes*, vol. 8, No. 1, pp. 17-22, (2001).
Burton, E.A., et al., "Multi-modal combination gene therapy for malignant glioma using replication-defective HSV vectors", *DDT*, vol. 6, No. 7, pp. 347-356, (2001).
Jacobs, A., et al., "HSV-1-Based Vectors for Gene Therapy of Neurological Diseases and Brain Tumors: Part II. Vector Systems and Applications", *Neoplasia*, vol. 1, No. 5, pp. 402-416, (1999).
Rosenfeld, M.R., et al., "Gene transfer of wild-type p53 results in restoration of tumor-suppressor function in a medulloblastoma cell line", *Neurology*, vol. 45, pp. 1533-1539, (1995).
Kagawa, S., et al., "Antitumor Activity and Bystander Effects of the Tumor Necrosis Factor-related Apoptosis-inducing Ligand (*TRAIL*) Gene", *Cancer Research*, vol. 61, pp. 3330-3338, (2001).
Frenkel, N., et al., "Minireview: The Herpes simplex virus amplicon—a versatile defective virus vector", *Gene Therapy*, vol. 1, pp. 540-546, (1994).
Kwong, A.D., et al., "Herpes simplex virus-infected cells contain a function(s) that destabilizes both host and viral mRNAs", *Proc. Natl. Acad. Sci. USA*., vol. 84, pp. 1926-1930, (1987).
Kwong, A.D., et al., "Herpes Simplex Virus Virion Host Shutoff Function", *Journal of Virology*, vol. 62, No. 1, pp. 912-921.
Todo, T., et al., "Viral Shedding and Biodistribution of G207, a Multimutated, Conditionally Replicating Herpes Simplex Virus Type 1, after Intracerebral Inoculation in *Aotus*", *Molecular Therapy*, vol. 2, No. 6, pp. 588-595, (2000).
Rainov, N.G., "A Phase III Clinical Evaluation of Herpes Simplex Virus Type 1 Thymidine Kinase and Ganciclovir Gene Therapy as an Adjuvant to Surgical Resection and Radiation in Adults with Previously Untreated Glioblastoma Multiforme", *Human Gene Therapy*, vol. 11, pp. 2389-2401, (2000).
Read, G. S. et al., "Herpes Simplex Virus Mutants Defective in Virion-Associated Shutoff of Host Polypeptide Synthesis and Exhibiting Abnormal Synthesis of α (Immediate Early) Viral Polypeptides", *Journal of Virology*, vol. 46, No. 2, pp. 498-512, (1983).
Romi, H., et al., "Tamplicon-7, a Novel T-Lymphotropic Vector Derived from Human Herpesvirus 7", *Journal of Virology*, vol. 73, No. 8, pp. 7001-7007, (1999).
Spaete, R.R., et al., "The Herpes Simplex Virus Amplicon: A New Eucaryotic Defective-Virus Cloning-Amplifying Vector", *Cell*, vol. 30, pp. 295-304, (1982).
Vlazny, D.A., et al., "Replication of herpes simplex virus DNA: Localization of replication recognition signals within defective virus genomes", *Proc. Natl. Acad. Sci. USA*., vol. 78, No. 2, pp. 742-746, (1981).
Rosenfeld, M.R., et al., "Gene transfer of wild-type p53 results in restoration of tumor-suppressor function in a medulloblastoma cell line", *Neurology*, vol. 45, No. 8, pp. 1533-1539, (Aug. 1995).

* cited by examiner

COMPOSITE ONCOLYTIC HERPES VIRUS VECTORS

CROSS-REFERENCE TO RELATED APPLICATIONS

This is a National Phase Application filed under 35 U.S.C. 371 of International Application No. PCT/IL2002/000345, filed May 2, 2002, claiming the benefit under 35 U.S.C. 119(e) of U.S. Provisional Application No. 60/287,717, filed May 2, 2001, the entire content of each of which is hereby incorporated herein by reference in its entirety.

FIELD OF TH INVENTION

The present invention concerns Herpes Simplex Virus (HSV) derived vectors and use thereof in the treatment of malignant diseases.

LIST OF REFERENCES

The following is a list of prior art publications referred to in the present specification.
Efstathiou S. et al., U.S. Pat. No. 5,928,913, 1999.
Frenkel N, Singer O and Kwong, A. D, *Gene Therapy* 1:540-546, 1994.
Kwong A. D. and Frenkel N. *Proc. Natl. Acad. Sci. USA* 84:1926-1930, 1987.
Kwong, A. D. and Frenker N, *J. Virol.* 62:912-921, 1988.
Kwong A. D. et al. *J. Virol.* 62:912-921, 1988.
Leib D. A., 1997 U.S. Pat. No. 5,698,431.
Markert, J. et al., Herpes 8:1, 2001.
Rabkin S. et al., *American Society of Gene Therapy*, Program No. 2046, 2000.
Ranov, N. G., *Gene Therapy* 11:2389-2401, 2000.
Read, G. S. and Frenkel N. J., Virol. 46:498-512, 1983.
Romi, H, Singer, O, rapaport, D and Frenkel, N, *J. Virol.* 73:7001-7007, 1999.
Spaete, R. R. and Frenkel, N, *Cell* 30:295-304, 1982.
Spear, M. A. et al., WO 0077167, 2000.
Vlazny, D. A. and Frenkel N, *Proc. Natl. Acad. Sci, U.S.A.,* 72:742-746, 1981.

The acknowledgement herein of the above art should not be construed as an indication that this art is in any way relevant to the patentability of the invention as defined in the appended claims.

BACKGROUND OF THE INVENTION

Cells infected with HSV-1 and HSV-2 (the facial and genital strains of HSV) are typically induced to express suicidal genes destined to destroy the cell prior significant viral replication. To overcome this effect and to secure the cell for viral replication, the virus undertakes an immediate counter attack by expressing the virion host shutoff (vhs) (UL41) gene—a 58 kDa structural component of the HSV-1 virion with a powerful mRNA destabilization/degradation activity. The vhs protein is shed into the cellular cytoplasm upon viral uncoating during viral entry into the cells (Read and Frenkel, 1983; Kwong et al. 1988; Kwong and Frenkel, 1987). Based on recent experiments, it seems that the vhs protein counteracts the cells' suicidal functions by immediate destabilization/degradation of the infected cell mRNAs, including house keeping genes and stress related suicidal genes induced post viral infection and may encode anti apoptotic genes. In consequence of the mRNA degradative activity host cell protein synthesis is shutoff, the suicidal proteins are not produced and the cells survive for a certain period of time, allowing viral replication before death of the target cell.

HSV-1 mutants carrying a mutation in the vhs gene have been developed. Whereas wild type HSV-1 infection is accompanied by host mRNA degradation HSV mutants which are deficient in the virion host shut-off (vhs) function ("vhs1 mutants") allow continued cell protein synthesis. One such mutant termed UL41NAB was developed which infection into cells was shown to be attenuated in its ability to replicate and reactivate from latency (Leib, D., 1997).

HSV derived amplicons comprising at least one inserted gene under control of a promoter in association with helper HSV have been disclosed (Spaete and Frenkel, 1982, Frenkel et al., 1994, Vlanzy, D. A. et al., 1981). In one example of such systems, the associated helper virus is of a restricted replication competence in a normal host cell (Efstathiou S. et al., 1999). In another example, the recombinant HSV vectors are modified to target and infect a selected cell type (Spear, M. A. 2000).

The incidence of brain tumors is estimated to be 5-14.1 per 100,000. Gliomas account for 40-60% of the primary tumors, 75% of which are malignant. Gliomas are the most common primary tumor arising in the human brain. Malignant gliomas account for 30% of primary brain tumors in adults, and are divided by grade into two categories, anaplastic astrocytoma and glioblastoma. The estimated incidence of malignant glioma in the United States is 14.7 per 100,000, representing approximately 10,000-15,000 new cases annually. Despite improved aggressive surgical therapy, radiotherrapy and chemotherapy, malignant gliomas are almost always fatal; the overall 5 year survival rate for glioblastoma, the most malignant glioma, is less than 5.5% and the median survival is approximately 52 weeks. These figures have remained virtually unchanged over the past three decades. Treatment of systemic tumors often fails because of development of central nervous system metastases. The advanced stage indicates no curability. Most gliomas have poor prognosis without any completely effective treatment Recently, HSV viral vectors were evaluated for their efficacy and safety in clinical use in humans. In one study, HSV derived vectors comprising HSV mutant viruses deficient in the gene encoding the 34.5 protein (a major determinant of neuropathology) were tested in patients with relapsed glioma. This mutant is a mutli-mutated conditionally replicating HSV vector termed "G207" which has deletions of both 34.5 loci and in the ICP6 (ribonucleotide reductase (RR)) which is required for replication in non-dividing cells (Rabkin, S. et al. 2000). The G207 mutant is now being tested in a Phase I Clinical Trial for recurrent glioblastoma in which it has been shown to be non toxic and without serious adverse events, but its efficacy has not yet been demonstrated. In addition, insertion of antineoplastic genes (specifically cytokine genes) into the mutated vector has been proposed (markert, J, 2001).

In another study an HSV type 1 thymidine kinase and gancyclovir gene therapy was evaluated as an adjuvant to surgical resection and radiation in adults with previously untreated glioblastoma multiform (Ranov, N. G., 2000). In a phase III trial patients with untreated glioblastoma multiform received either standard surgical and radiotherapy or standard therapy plus adjuvant gene therapy during surgery. Clinical safety of the treatment was determined and was comparable in both groups but there were no significant clinical differences between gene therapy and control patients.

HSV derived viral oncolytic vectors having high efficacy for treatment of human tumors yet maintaining their safety are desired.

SUMMARY AND GENERAL DESCRIPTION OF THE INVENTION

In order to provide a safe and highly efficient HSV derived vector for the treatment of a malignant disease, it is desired to provide in such a vector at least a dual viral weaponry which will enhance the chance of eliminating a target tumor cell yet remain safe in that it is designed not to replicate in non-dividing non malignant cells.

In accordance with the Invention, such a composite vector is provided. The HSV-derived vector of the invention comprises two main components: one component which is a defective viral genome with multiple reiterations of amplicon type repeat units each carrying inducible toxic genes with cell destructive capabilities ("the amplicon") and as a second component an HSV mutant helper virus which is incapable of replication in non-dividing cells or at least has a significantly low replication capacity in such cells ("the helper virus"). Such a composite vector in accordance with the invention will be referred to herein at times as the "Composite oncolytic vector".

Preferably, the helper virus is mutated in the virion host shut-off (vhs-UL41) genes. Most preferably, the helper virus is double mutated both in the vhs gene as well as in the ribonucleotide reductase (RR) genes.

The dual viral arms of such a vector substantively enhance the efficacy of the vector while maintaining its safety. The dual components of the vector of the invention which attack the target malignant cell both by effective expression of cytotoxic foreign genes on the amplicon which are expressed in many copies in a short period of time as well as by the ability of the mutated helper to drive the cell to cell death (apparently by inducing apoptosis), substantively enhance the efficacy of the vector while maintaining its safety. The term "enhanced efficacy" should be understood to mean an efficacy which is higher than the efficacy of only one component of the vector (i.e. the amplicon comprising the toxic gene or helper vector).

Such a composite oncolytic vector comprising a combination of amplicons and mutants of HSV have not been described.

In accordance with one aspect of the invention, a pharmaceutical composition for use in the treatment of a solid tumor in an individual comprising an effective amount of an HSV derived amplicon defective viral genome carrying at least one toxic foreign gene and an HSV-derived mutant helper virus and a pharmaceutically acceptable carrier, excipient or diluent.

The term "effective amount" relates to an amount of each of the HSV derived viral components which will, upon administration to the individual, achieve the desired therapeutic effect. With regards to the amplicon, an effective amount will be such which results in a desired amount of expression of the foreign toxic gene in a short period of time. The effective amount of the helper component will be such that enhances the effect of the amplicon (by providing the necessary functions for gene expression) and preferably an amount which renders the helper virus cytotoxic to the cell. Wherein the helper virus is the vhs mutant, the effective amount will be such which leads to death of the target cell.

In the amplicon component of the composite vector, the defective genomes are engineered to carry foreign toxic genes. The term "foreign toxic genes" relates to genes which are not naturally expressed by the target cells and are designed to destroy the cells in a controlled fashion. Any such toxin gene may be used in accordance with the invention, and the gene may be chosen by a person versed in the art on the basis of the kind of tumor to be treated as well as additional factors. An example of such toxic gene in an amplicon is the gene encoding the thymidine kinase (TK) which when expressed in the cells renders them sensitive to ganciclovir, producing complete inhibition of host DNA replication and the destruction of the dividing cells. Other types of toxic foreign gene to be placed in the amplicon are, for example, tumor necrosis factor (TNF), TNF related apoptosis inducing ligand (TRAIL), and P53. Such toxic genes can be put under the control of the Tet On system, allowing the expression of the toxic genes only when treated with tetracycline. Other toxin genes may be constructed to be expressed under control of other suitable promoters or inducers. The amplicon in accordance with the invention may also comprise a number of toxic genes under the control of one or more promoters. Such toxic genes may also be constructed under control of cell or tissue specific promoters which are expressed only in the desired cell or tissue (e.g. a promoter which controls expression of a prostate specific antigen (PSA) only in prostate cells).

The invention also provides use of an HSV derived amplicon defective viral genome carrying at least one toxic foreign gene and an HSV-derived mutant helper virus for the preparation of a pharmaceutical composition for the treatment of a solid tumor in an individual.

In accordance with another of its aspects, the present invention provides a method for the treatment of an individual having a solid organ tumor comprising administration of an HSV derived viral vector comprising an effective amount of a combination of an HSV derived amplicon defective viral genome carrying at least one toxic foreign gene and an HSV-derived mutant helper virus. Preferably, the helper virus comprises a mutation in the vhs gene. Most preferably, the mutant helper virus carries also a mutation in the RR genes.

The term "treatment" in accordance with the invention should be understood to mean any alleviation of a condition of a patient suffering from a solid tumor. Such alleviation may be a reduction in the size of the tumor, reduction in the rate of growth of the tumor, alleviation of tumor-related symptoms, prevention of metastasis, etc.

By a preferred embodiment, the helper virus in accordance with the invention is constructed to carry a mutated virion host shutoff (vhs) gene such a vector is at times referred to as "vhs mutant". The cytotoxic effect of the vhs mutant virus was shown to be associated to induction of pronounced cell apoptosis in the infected cells. In addition, due to the mutated vhs gene, the transcribed mRNA of the toxic gene carried by the amplicon component of the composite vector is not immediately disintegrated and inactivated (as in the case of the non-mutated vhs gene), thus enabling expression of the toxic gene and enhancement of the apoptopic effect of the vhs component, resulting in enhanced efficacy of the composite vector as a whole.

The helper virus in accordance with the invention may also comprise a mutation in the RR gene. The RR enzyme is essential for viral replication in resting, non-dividing cells, whereas the virus can use the cellular RR which is active in growing cells. The RR mutation has been introduced in the small RR subunit ($I_L$ 39 gene) of the enzyme. This renders it inactive. The use of RR mutation has the vector safer for use in gene therapy, by not allowing any replicating virus to spread to neighboring normal cells. The helper vector may contain the RR mutation alone or together with the mutant vhs. Although, (as shown in FIG. 3 below), growth of the vhs mutant in neuronal cells is limited to make the vector safer, introduction of the RR mutant into the vhs helper machinery will make it even safer for potential use in gene therapy.

The two components of the composite vector of the invention may either be obtained by infecting cells with the helper virus and transfecting the same cells with amplicon plasmids or, by dual transfection of cells with helper virus DNA and amplicon plasmid followed by repeated serial propogation of the virus and amplicon mixture to generate a stock of cells comprising both components which can be then administered to the individual. Alternatively, the amplicon may first be grown in cells of a cell line which comprises non infectious vhs mutated HSV helper viruses lacking the Pac-1 and Pac-2 signals and thus not being able to be packaged. In this manner, it is possible to prepare large quantities of the amplicons ex vivo without infectious helper viruses, resulting in an amplicon packaged in the virions of the vhs mutant virus. Such packaged amplicons are infectious, i.e. they can enter into the cells and introduce both the foreign cytotoxic genes as well as the vhs-1 mutant gene. Such amplicons may be administered to the individual without a helper virus, i.e. both components of the vector of the invention will be present in the packaged amplicons.

The HSV derived, composite oncolytic vector of the invention has a wide host range including epithelial, fibroblastic and neuronal cells and thus is suitable for the treatment of various solid organ tumors such as, for example, brain malignancies including neuroblastoma and glioblastoma multiform, lung, pancreatic, kidney, colon and stomach cancers.

Typically, in accordance with the invention, the vector will be administered to the individual by local injection directly into the tumor. However, at times components of the vector may also be administered by other administration routes including systemically, intraveneously (i.v.), subcutaneously (s.c.), intramuscular (i.m.), intraperitoneal (i.p.) or orally. Such components will be prepared in any of the formulations known in the art suitable for the specific route of administration chosen by the person versed in the art.

The HSV derived composite vector of the invention will typically have the following characteristics: (Spaete and Frenkel, 1982, Frenkel et al, 1994)

(i) The HSV amplicon is a versatile vector which can target fibroblastic, epithelial and neuronal cells.

(ii) The system consists of a helper virus and constructed defective genomes, which contain multiple reiterations of the amplicon DNA sequences.

(iii) Two cis acting signals are required for amplicon propagation in the presence of a helper virus: a DNA replication origin and the cleavage packaging signals.

The amplicon can use either the OriS or the OriL replication origins.

(iv) The defective virus genomes replicate by the rolling circle mechanism, which yields "endless" concatemeric DNA molecules, with multiple head to tail repeats of the amplicon sequences, including the cloned transgene sequences.

(v) The helper virus supplies, in trans, the DNA replication and packaging machinery including replication enzymes (e.g viral DNA polymerase, helicase, primase, ligase and DNA binding proteins) and the packaging functions, including the proteins and glycoproteins of the HSV virion.

(vi) The long replicated DNA concatemers are cleaved during the packaging process. In HSV the cleavage/packaging signals "pac-1" and "pac-2" are present in the a sequences.

(vii) The cleaved DNA molecules range in size from a single to multiple repeat units, corresponding in their overall size from the size of individual amplicons up to the intact HSV-1 genome (152 kb). To determine the details of the cleavage/packaging process we have analyzed by pulse field electrophoresis the viral DNA molecules present in cells, which received different size amplicons. The results of these experiments have shown that cleavage/packaging had also involved a headful constraint with the majority of packaged molecules spanning in their size approximately genome length DNAs in the range of 136-150 kb. Cleavage take place as the viral genomes are "fed" into the structural virion in the process of packaging.

(viii) The precise location of the cleavage and consequent packaging is determined by the pac-1 and pac-2 signals which are well conserved in all the herpesviruses (Romi et al., 1999). It has been shown that cleavage occurs 40-44 bp from the pac-1 signal, and 30-35 bp away from the pac-2 signal.

(ix) The pac-1 and pac-2 elements are also required for packaging of the helper virus. The repeat units of the HSV-1 defective genomes can reach 17 kb in their size. Viral amplicons of larger size are randomly deleted in the process of DNA replication, until the repeat unit size reaches 17 kb (Kwong and Frenkel, 1985). Defective virus genomes containing repeats of sizes smaller than 17 kb can be stable propagated in virus stocks for more than 50 sequential passages.

The HSV derived amplicon may also carry a marker gene which enables detection of the vector. Such a gene may be any of the known marker genes such as, for example, the green fluorescence protein (GFP) marker genes.

In accordance with the invention, the composite oncolytic HSV derived vector comprising the two above described components may be administered to an individual in combination with additional treatments or components. One such component may, for example, be an additional viral vector comprising a gene encoding a peptide which enhances the immune activity of the treated individual. An example of such a vector is one capable of infecting lymphotropic cells such as a herpes virus 6 (HHV-6) or HHV-7 derived amplicon (Romi et al., 1999) containing the "immunogenic" gene. The immunogenic gene may for example be a gene which encodes for an interleukin such as IL-2, IL4, IL-10 or Interferon and, upon administration, enhances the expression of such peptides in the cells. The "immunogenic" vector may be administered in various combinations with the HSV-derived vectors. The additional component may be administered to the individual by any of the administration routes described above and at various times before, during or after administration of the composite oncolytic HSV derived vector.

Thus the present invention further provides a combination of two pharmaceutical compositions including a first pharmaceutical composition comprising an effective amount of an HSV derived defective viral amplicon genome carrying at least one toxic foreign gene together with an HSV-derived mutant helper vector and a second pharmaceutical composition comprising an effective amount of an viral derived amplicon carrying a gene encoding for a peptide capable of enhancing the immune system of the treated individual, the combination intended for administering to the individual for treatment of a solid tumor, in which treatment said second composition is administered at time T, said time T being before, during or after administration of said first pharmaceutical composition.

The above combination may be in the form of a package including said first and said second pharmaceutical compositions.

The invention further provides a method for the treatment of a solid tumor in an individual comprising administering to said individual an effective amount of a first pharmaceutical composition comprising an effective amount of an HSV derived defective viral amplicon genome carrying at least one toxic foreign gene together with an HSV-derived mutant helper vector and at time T before during or thereafter administering to said individual a second pharmaceutical composition comprising an effective amount of a viral derived amplicon carrying a gene encoding for a peptide capable of enhancing the immune system of the treated individual.

The invention further provides use of a first pharmaceutical composition comprising an effective amount of an HSV derived defective viral amplicon genome carrying at least one toxic foreign gene together with an HSV-derived mutant helper vector for the treatment of a solid tumor in an individual, which treatment includes administering to the individual said first composition and at a time T before, during or thereafter, administering to said individual a second pharmaceutical composition comprising an effective amount of a viral derived amplicon carrying a gene encoding for a peptide capable of enhancing the immune system of the treated individual.

Yet further, the invention provides a kit comprising a first pharmaceutical composition comprising an effective amount of an HSV derived defective viral amplicon genome carrying at least one toxic foreign gene together with an HSV-derived mutant helper vector and a second pharmaceutical composition comprising an effective amount of a viral derived amplicon carrying a gene encoding for a peptide capable of enhancing the immune system of the treated individual, together with directions for use.

Furthermore, the additional treatment administered to the treated individual may be any other treatment typically administered to individuals having a solid tumor, such as for example, treatments intended to enhance the level of immune response (e.g. Interferon) or treatment and targeting of the tumor cells such as radiation or chemotherapy.

In the following, the invention will be exemplified with reference to the following non limiting examples.

EXAMPLES

Example 1

Materials and Methods

Figure 1:
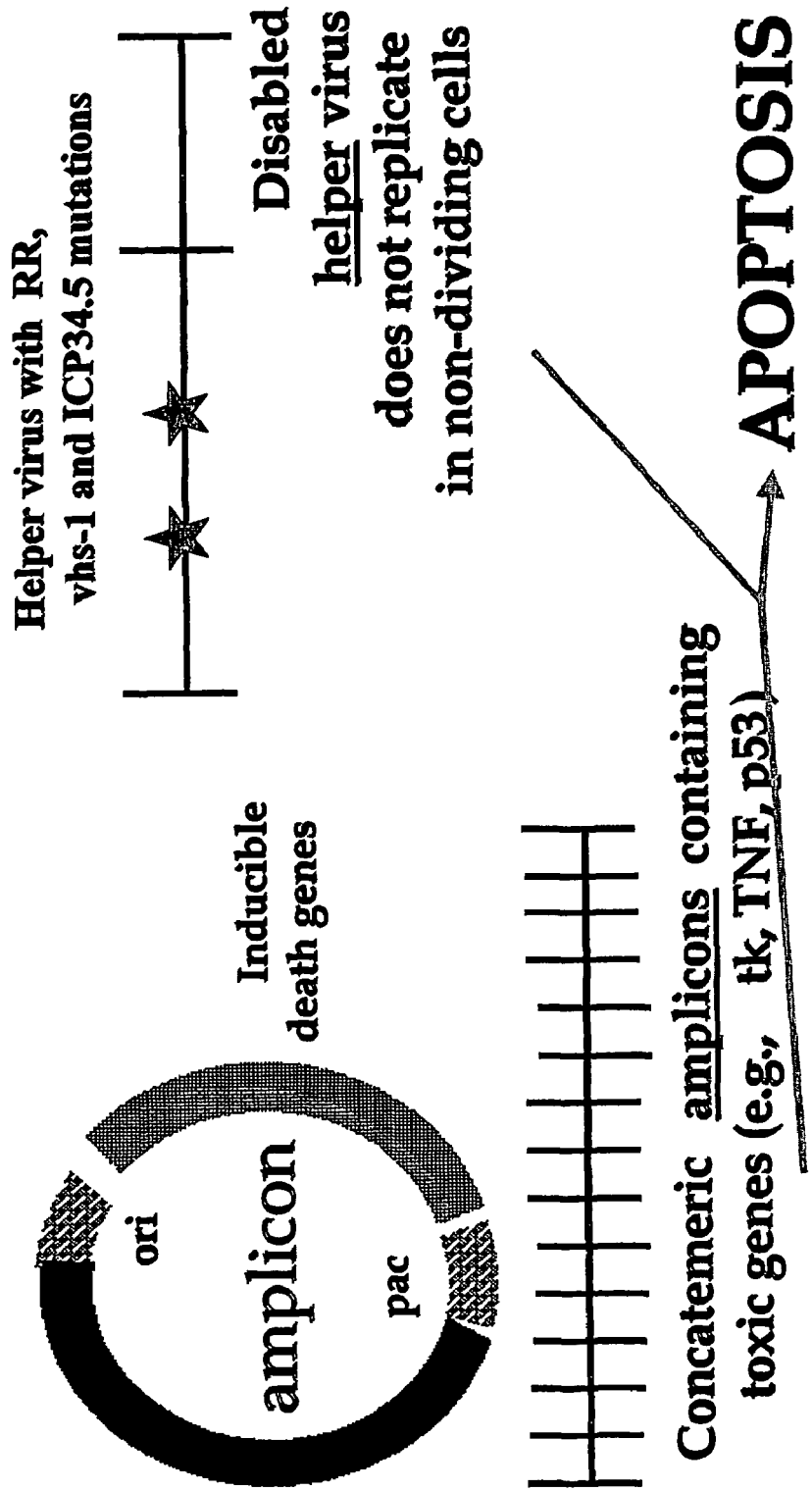
FIG. 1 is a schematic representation showing an example of the two components of the composite oncolytic HSV-1 derived vector of the invention. One component shown is an HSV-1 amplicon carrying multiple reiterations of at least one toxic gene and the second component is a mutant HSV-1 derived helper virus with replication capacity in dividing cells and carrying a mutation in the virion host shutoff (vhs) function which induces cellular suicidal death functions as well as a mutation in the ribonucleotide reductase (RR) gene.
Figure 2:
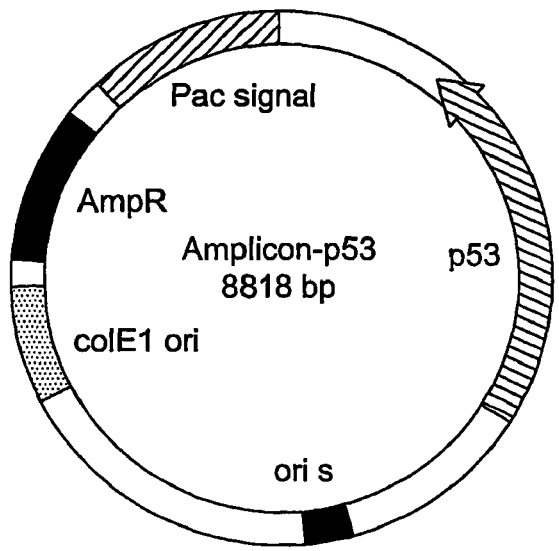
FIG. 2 is a schematic representation showing an example of one component of the composite oncolytic vector of the invention being an HSV-derived oncolytic HSV-1 amplicon carrying the p53, a viral origin of replication (ori) and packaging signals (pac).

Cell cultures:—Primary cultures highly enriched for cerebellar granular neurons were prepared from 8 days old BALB-C mice. Cultures were made from mouse brains. The cells were trypsinized and plated on dishes coated with poly-L-lysine in standard medium (basal medium Eagle's, 10% fetal calf serum, 25 mM KCl, 2 mM glutamine, 50 µg/ml gentamycin and 250 ng/ml amphotericine B supplemented with 1 mg/ml glucose. Cytosine-β-arabinofuramoside (Ara-C) (10 µM was added to the medium 18-22 h after plating to prevent replication of non neuronal cells.

Viruses:—HSV-1 (KOS) served as the wild type virus. The virion associated host shutoff mutant was derived in our laboratory from −1 (KOS) by general BudR mutagenesis and selection of mutants which did not shutoff host protein synthesis in the presence of actinomycin D to reassure that this is a virion function brought into the cells within the infecting virions (Read and Frenkel, 1983). Virus stocks were made with limited passaging, employing Vero cells at an input multiplicity of infection (m.o.i.) of 0.01 pfu/cells.

HSV infection of cerebellar granule cells:—The granule neurons were infected four days after plating the neurons. The number of viable cells was determined each experiment, employing trypan blue exclusion assay. The neurons were washed twice with conditioned medium to remove the Ara-C and then exposed to the appropriate virus m.o.i., as stated in the text. Infection was in 199V medium with 1% fetal serum. The cells were infected for two hours at 37° C. The innoculum was then removed and conditioned medium added prior to further incubation at 37° C.

Assay of infectious virus yield:—At different times p.i. the infected cerebellar granule neurons were harvested and disrupted by three cycles of freezing and thawing, to release the virus. Infectious virus was titered by plaque assays in Vero cells.

Trypan blue viability assay:—Neuron survival was determined by trypan blue exclusion assay. Cells were incubated for 10 min in a solution of 0.1% of trypan blue in phosphate buffer saline (PBS), pH-7.4 and then washed twice with PBS. Three randomly chosen fields which contained approximately 500 cells each were analyzed by phase-contrast and bright field microscopy. Cells excluding the dark blue dye were counted as viable, whereas blue-stained cells were scored as dead.

MTT assay:—A modification of previously described procedure was used: neuronal cultures (in 96 well plates) were incubated for 60 min. at 37° C. with 0.5 mg/ml MTT in standard medium. The MTT solution was aspirated and the cells were lysed in 200 ml DMSO. The amount of MTT formazan was quantified by determining the absorbency at 490/690 in a Bio-tek microplate reader (Wiooski, Vt., USA).

DNA staining with DAPI:—Cells were grown on glass cover slip coated with poly-1-lysin. The cells were infected. Upon completion of the experiments, the cells were washed with phosphate saline buffer pH-7.4 (PBS) and fixed for 10 min in 4% formaldehyde (in PBS). After fixation the neurons were washed with PBS, stained for 5 min with 10 μg/ml DAPI (4,6-diamino-2-phenylindol), and washed twice with PBS; a drop of either N-propyl gallat or glycerol was added to enhance fluorescence, which was detected by UV light microscopy. When completed the cells were washed with PBS and fixed in 45 formaldehyde in PBS. After fixation and washing stained with 10 mg/ml DAPI (washed, and a drop of glycerol was added to enhance the fluorescence which was detected by UV light microscopy.

Results

Figure 3A:
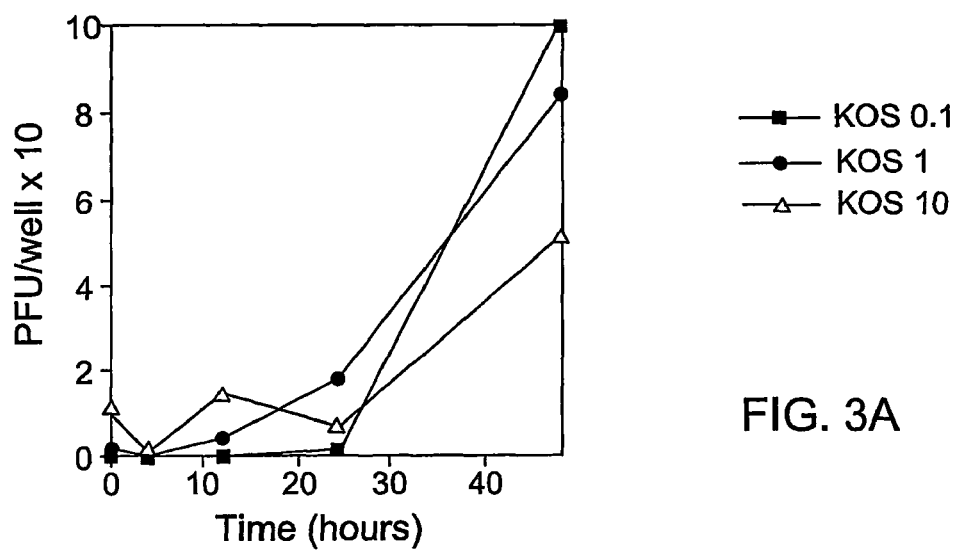
FIG. 3 is a schematic representation showing the replication of a vhs-1 mutant helper virus after infection into mouse cerebral granular neurons as compared to a wild type HSV (KOS) vector infected into such cells. The replication was measured at different multiplicities of infection (m.o.i.) and at different times after infection.
Figure 3B:
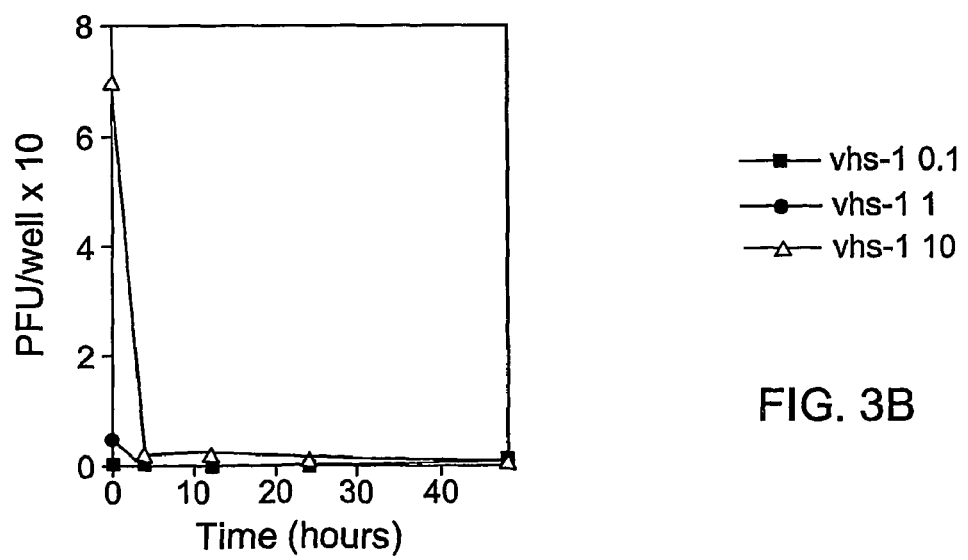

The Replication of Wild Type (Wt) and Vhs-1 Mutant Viruses in Mouse Cerebellar Granule Neurons:

The replication of wt HSV-1 (KOS) and the vhs-1 mutant viruses in mouse cerebellar granule neurons, was analyzed at different multiplicities of infection (m.o.i.)s. FIG. 3 compares infectious virus yield in the neuronal cells up to 48-hrs post infection (p.i.) with input m.o.i. of 0.1, 1 and 10 PFU/cell. Titration of the resultant virus stocks was done in Vero cells. The results have shown that the wt virus replicated productively in the neuronal cells. Infectious virus yield was highest in the cultures infected with an input m.o.i. of 0.1 pfu/cell (1428 fold amplification of the input virus). They were lower with the input m.o.i.s of 1 and 10 PFU/cell (62 and 4.6 fold amplification of the input virus, respectively, by 48 hrs p.i. In contrast, the vhs-1 mutant did not replicate well in the neuronal samples, with infectious virus yield corresponding to 2 fold-input virus in cells infected with 0.1 PFU/cell vhs-1 mutant virus and no amplification of virus in cells infected with 1 and 10 PFU/cell respectively. Based on the data it can be concluded that the vhs-1 mutant posses only limited capacity to replicate in the brain cells.

Figure 4:
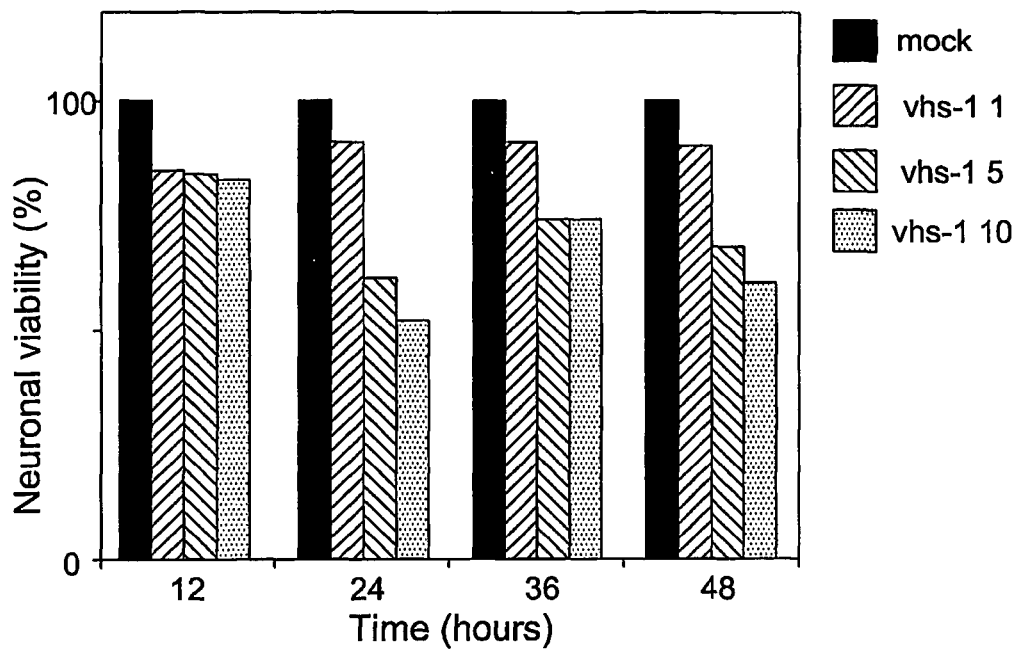
FIG. 4 is a graphic representation showing the viability of non infected mouse neuron cells (mock-control) and mouse neuron cells following infection with the vhs-1 mutant vector in different multiplicities of infection at different times after infection of the cells and as measured by the MTT assay.

The Induction of Programmed Cell Death (Apoptosis): MTT Assays:

Because the vhs function causes destabilization/degradation of host cell mRNAs it was of interest to determine whether the infected cells were induced to undergo into a programmed cell death, and whether the vhs-1 mutant was more toxic to the cerebellar granule neurons. Duplicate 96 well cultures of the purified cereberal neuron cultures were infected with HSV-1 (KOS), or the vhs-1 mutant viruses. Cell viability was measured by MTT formazan incorporation at 12, 24, 36 and 48 hrs p.i., quantified by 490/690 absorbency in Bio-tek microplate reader. The experiment was repeated several times with similar results employing different input m.o.i.s An exemplary experiment involved infection of 96 well monolayers of purified granular neurons cultures at input m.o.i. of 1, 5 and 10 PFU/cell of HSV-1 (KOS) or the vhs-1 mutant viruses. As shown in FIG. 4.

Whereas the neuronal infection with the wt HSV-1 (KOS) did not cause apoptosis by 48 hrs p.i., the vhs-1 mutant virus infection was accompanied with pronounced (down to 50%) apoptosis.

Figure 5:
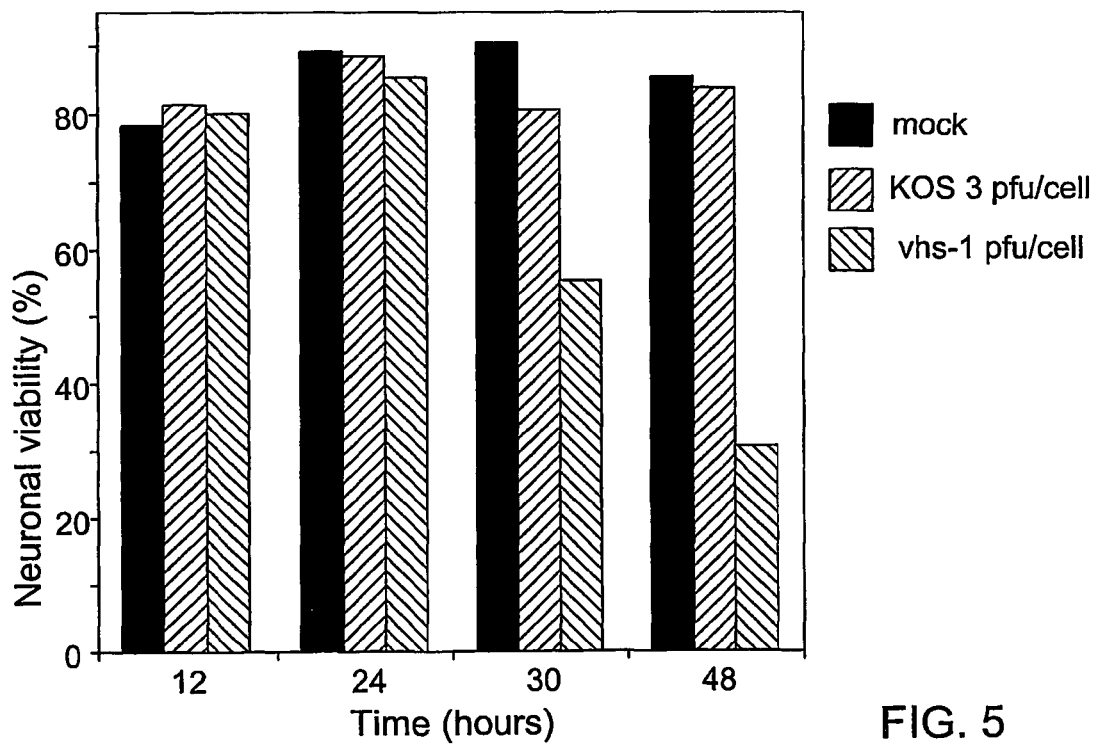
FIG. 5 is a schematic representation showing the viability of neuron cells after infection of the cells with either a HSV derived vector (KOS) or a vhs-1 mutant vector at various times after infection of the cells and as measured by the trypan blue assay as compared to non infected (mock) control cells.

Trypan Blue Assay:

In parallel to the MIT assay neuronal viability was determined by trypan blue exclusion assay. Cells excluding the dark blue dye were counted as viable, whereas blue-stained cells were scored as dead. As shown in FIG. 5, whereas KOS virus infection at m.o.i. of 3 PFU/cell did not cause substantial cell death by 48 hrs p.i., close to 50 and 70% death of neuronal cells have died in the vhs-1 infected cultures.

Characterization of Cell Death: DAPI Assays

Figure 6:
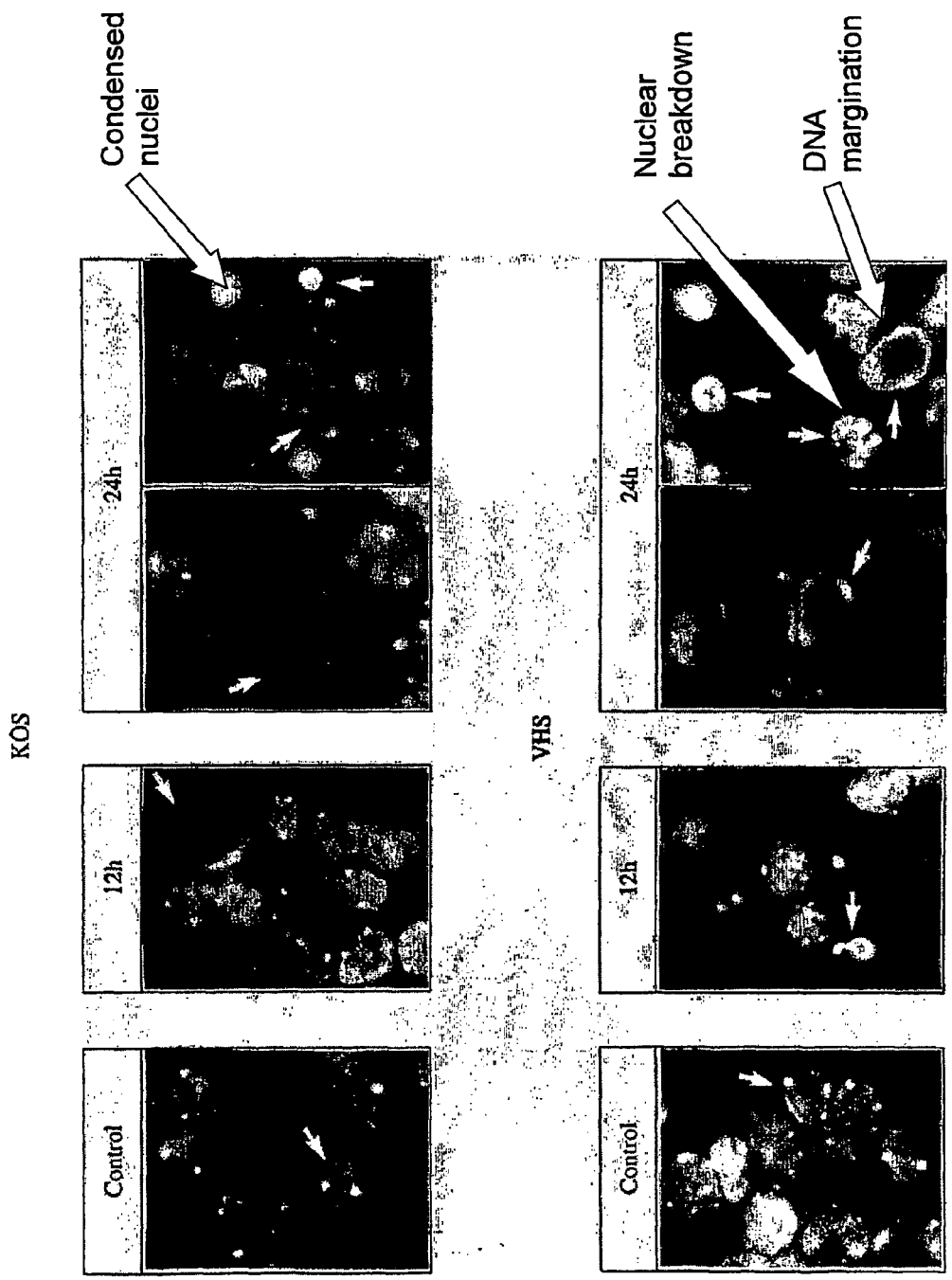
FIG. 6 shows photographs of mouse neuronal cell cultures infected with the KOS or vhs-1 viral vectors at various times after infection and DAPI staining. Apoptosis is seen in the vhs-1 infected cells.

To examine whether the infection produced apoptotic death, the neuronal is cultures were grown on a cover slip, with poly-L-lysin support. Following infection with wt and vhs mutant viruses for different length of time the cells were fixed with formaldehyde, stained with DAPI (4,6-diamino-2-phenylindol) and examined in the fluorescent microscope. FIG. 6 shows that nuclei of uninfected granule neurons appeared uniform in size, with an oval shape, and were rather homogeneously stained with moderate intensity and spotted with glowing areas, typical of mouse cells. Twelve hours after exposure to KOS the cells appeared unchanged whereas in the cells exposed to vhs viruses, some neurons' nuclei lost their oval shape and appeared like bright round spots. As the death process progressed, the number of the disintegrated nuclei (round compartments) increased. Twenty-four hours after exposure to vhs viruses, all the nuclei of the underwent margination, fragmentation and condensation into individual particles while some of the KOS exposed cells showed first signs of the deterioration process. These results are indistinguishable from the observations of the DAPI staining of cerebral granule neurons deprived of high potassium, which leads to apoptotic neuronal death. Taken together, our results show that virus infection-induced death has apoptotic characteristics.

The effect of viral infections on degradation of mRNA of house keeping genes as well as stress related genes induced post infection (such as tubulin and the heatshock 70 proteins (HSP-70)), in mock infected cells or in cells infected with HSV-1 (KOS), HSV-2 (6) and the vhs-1 mutant was analyzed (results not shown). Several conclusions can be drawn from this exemplary experiment: (i) the vhs function does not require viral gene expression post-infection inasmuch as mRNA degradation occurs also when the cells were infected in the presence of actinomycin D, preventing altogether the transcription of host viral genes post-infection. (ii) The vhs function degrades genes such as tubulin. (iii) The heatshock "stress" mRNA was induced post-infection 70 protein which is induced in response to viral infection. Actinomycin D treatment prevented its accumulate in KOS and vhs-1 mutant virus infection.

As shown in the above figures, the above experiments employing cerebellar granule neurons of 8 day old BalbC mice show that: (i) the wt virus replicates well in the cerebellar granule neurons whereas no replication of the vhs-1 mutant occurred even by 48 hours post Infection (ii) wt virus infection does not induce apoptosis whereas mutant virus infection has induced pronounced cell death as measured by mitochondrial MIT (3-(4,5-dimethylthiazol-2-yl)-2,5-diphenltetrazolum bromide) assays of cell viability (iii) Similarly, trypan blue assays revealed no cell death following wt virus infection, compared to pronounced death at the vhs-1 infection. (iv) The neuronal cell death reflected apoptosis associated with cell deterioration and nuclei breakage as judged by Dapi fluorescence. The vhs-1 mutant virus infection causes more pronounced apoptosis and earlier that the limited apoptosis caused by the wt virus.

The above results also show that wt virus inhibits host gene expression post infection by letting the vhs RNase start destabilization/degradation of infected cell mRNAs including the host death genes induced in response to viral infection. In contrast, the cellular mRNAs are expressed efficiently in vhs-1 mutant virus infection, resulting in pronounced apoptosis. As noted above cell survival was advantageous for virus replication and whereas wt virus which did not cause apoptosis replicated well in the cerebellar neurons the vhs-1 mutant, which kills the cell, did not replicate in mouse neurons even by 48 hours post infection.

Example 2

Materials and Methods

H1299 human lung carcinoma cell line cells were infected with HSV-1 mutants (exemplified by vhs-1, γ34.5 and the 34.5, vhs double mutant) at multiplicity of infection of 1 and 10 pfu/cell. In lung cells, the helper virus must carry a mutation which prevents its replication in order to be safe. The number of viable and dead cells were determined at 14, 24, 36, 48, 72 and 96 hours post infection by typan blue assay.

Trypan Blue Assay

The cells were incubated 1 min. in a solution containing 0.1% of trypan blue in phosphate buffer saline. Then 500 cells were counted by bright field microscope. Cells excluding the blue dye were counted as viable, whereas blue stained cells were scored as dead.

Results

Figure 7A:
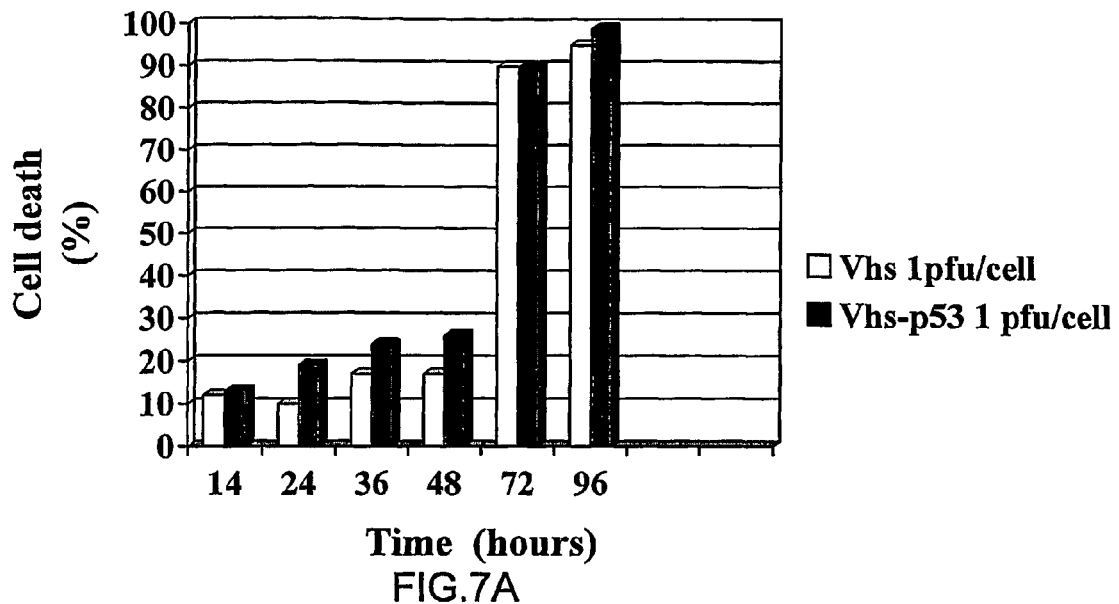
FIG. 7 is a schematic representation showing the percent of cell death of H1299 human lung carcinoma cells infected with the vhs-1 mutant helper virus alone or in combination with a HSV-1 amplicon vector carrying the p53 gene. The vectors were infected at a multiplicity of infection of 1 plaque forming unit (pfu)/cell (FIG. 7A) and 10 pfu/cell (FIG. 7B) and the number of viable dead cells were determined at various times after infection by the trypan blue assay.
Figure 7B:
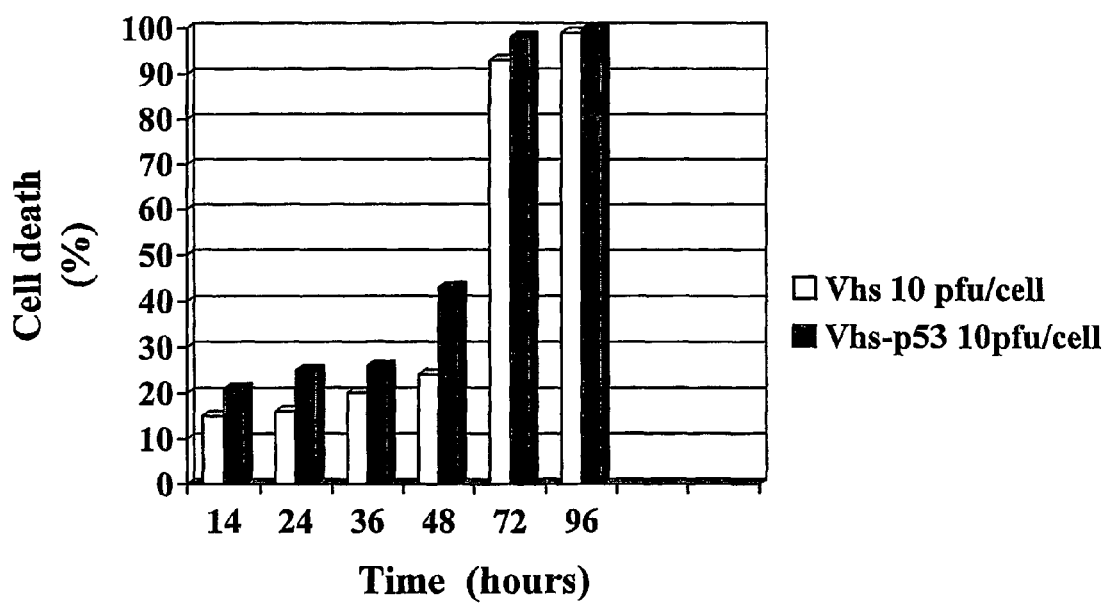
Figure 8A:
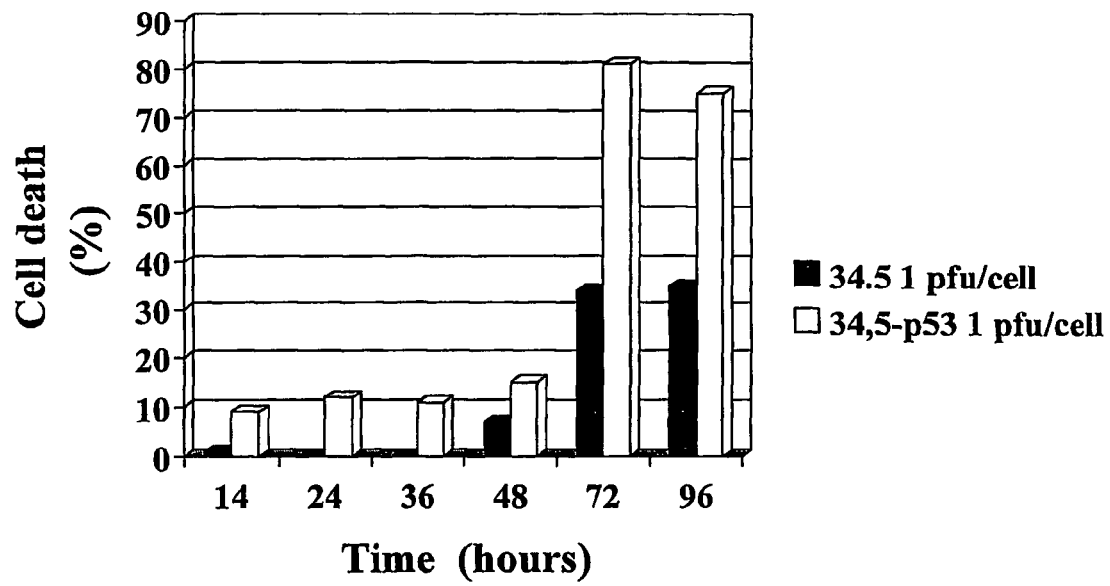
FIG. 8 is a schematic representation showing cell death of H1299 human lung carcinoma cells after infection with an HSV derived vector carrying the 34.5 mutation alone or in combination with an HSV-1 derived amplicon comprising the p53 gene in a multiplicity of infection of 1 pfu/cell (FIG. 8A) or 3 pfu/cell (FIG. 8B) at various times after infection of the cells and as determined by the trypan blue assay.
Figure 8B:
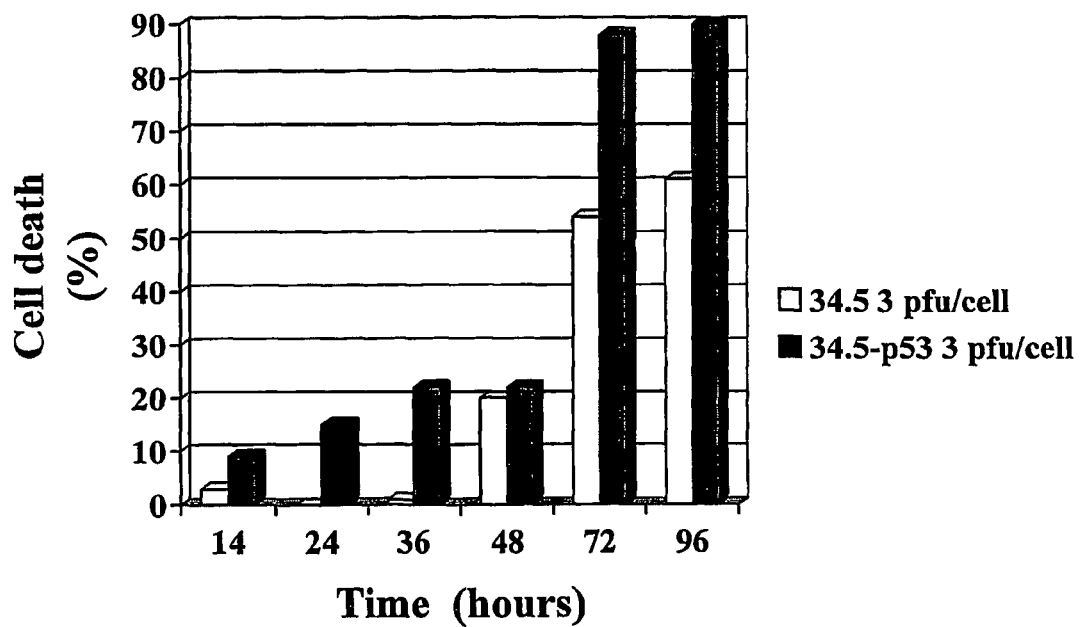
Figure 9A:
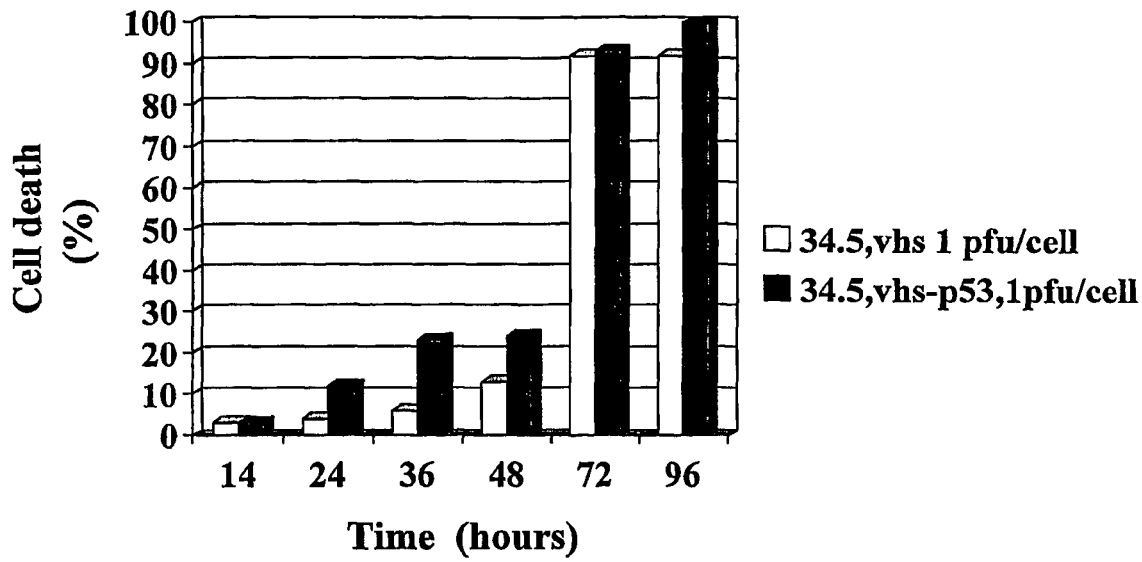
FIG. 9 is a schematic representation showing the viability of H1299 human lung carcinoma cells after infection with the doubly mutated HSV-1 vector carrying the 34.5 and vhs mutant genes in combination with an HSV-1 amplicon carrying the p53 cytotoxic gene at a multiplicity of infection of 1 pfu/cell (FIG. 9A) or 10 pfu/cell (FIG. 9B) at various times after infection of the cells and as determined by the trypan blue assay.
Figure 9B:
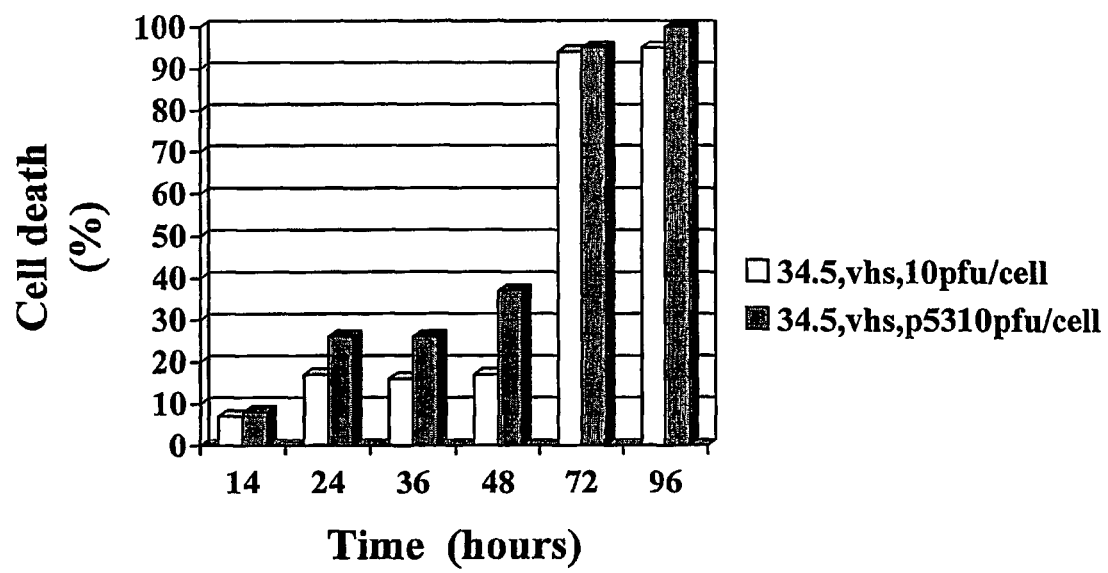

The results are shown in FIGS. 7-9 and can be summarized as follows:
(1) Good expression of the p53 gene (in all the samples containing the amplicon) in the lung cells is shown in the Western Blot in the human lung carcinoma cells.
(2) Concerning cell death in the infections:
  (i) The vhs-1 infections (FIG. 7) at 1 (FIG. 7A) and 10 (FIG. 7B) pfu/cell resulted in pronounced cell death operating exponentially, peaking at 3 and 4 days post infection (90, and 93% cell death respectively).
  (ii) The addition of the p53 containing amplicon increased cell death: as shown in the figures, the dual infections of the vhs-1 helper and the p53 amplicon resulted at each time point with increased cell death (e.g. 2 days post infection (p.i.) there was 20 and 40% cell death in the cultures infected with vhs and vhs+p53 respectively).
  (iii) As shown in FIG. 8, infection with the 34.5 at 1 and 10 pfu/cell resulted in incomplete death, which gradually increased reaching 30% death at the 1 pfu/cell infection, and 60% death at the 3 pfu/cell infection. The death was slowly plateauing at 3 to 4 days post infection.
  (iv) Dual infection of the cells with the 34.5 mutant helper and the p53 amplicon resulted in significantly increased death. Death increased exponentially between 2 and 3 days post infection reaching 88% at 3 days p.i. and reaching a plateau at 90% at 4 days p.i.
  (v) As shown in FIG. 9, the lung carcinoma cells infected with the double mutant 34.5×vhs underwent exponential cell death already between 2 and 3 days p.i. Death was 10% by 2 days post infection and increased exponentially to 90% by 3 days p.i.
  (vi) Death increased more rapidly and reached additional efficacies by the addition of the p53 amplicon reaching 93 and 100% 3 and 4 days p.i. respectively.
(3) Similar results were obtained using an MTT assay (measuring cell viability by the functionality of mitochondria) (not shown).

Example 3

HSV-1 amplicons containing the thymidine kinase (tk) gene were constructed. The amplicon is infected into various cells and tk gene expression in the in infected cells is evaluated by Western Blot analysis as described above.

In addition, gancyclovir induced death of the cells infected with the tk comprising amplicon alone or in combination with an HSV helper virus containing a mutated hvs gene is evaluated using the trypan blue or MTT assays as described above.

Example 4

An HSV-1 amplicon containing a gene encoding TNF has been constructed. The expression of the TNF gene in various infected cells as well as cell death of cells infected with the TNF comprising amplicon alone or in combination with an HSV derived helper vector containing a mutated hvs gene is evaluated as described above.

Example 5

In Vivo Effect of the HSV vhs Mutant Vector on Growth of Tumors in Vivo

Nude mice are injected subcutaneously with cells of a human glioblastoma cell line. At various stages of growth of the tumors, the mice are divided into the following groups:
(a) control mice receiving mock injections.
(b) mice receiving injections of the vhs-1 mutant HSV vector;
(c) mice receiving injections of a combination of the HSV amplicon carrying one or more toxic genes and the vhs-1 mutant HSV helper virus;
(d) mice receiving injections of the pure HSV amplicon devoid of infectious helper virus but carrying one or more toxic genes and the vhs-1 mutant protein in the virion encapsulating the amplicon (grown in cells comprising a pac-1, pac-2 deleted and vhs mutant helper virus);
(e) mice receiving each of the treatments of (a)-(d) together with a systemic infection of an HVV-6 or HVV-7 derived amplicon containing an IL-2 encoding gene at various times before, together with or after the injection of the HSV vectors.

The viral vectors are injected directly into the tumors of the mice and the development of the tumors in each of the groups is determined at various times after injection and compared to the development of the tumors in the control group.

In an additional in vivo experiment, the above-mentioned vectors are injected into tumors developed from pancreatic malignant cells or long malignant cells in nude mice, as another example to highly malignant tumors within internal organs.

The invention claimed is:

1. A pharmaceutical composition for the treatment of a solid tumor in an individual, comprising:
   an effective amount of an HSV1 amplicon defective viral genome comprising at least one toxic foreign gene selected from the group consisting of thymidine kinase (TK) and/or P53 and an HSV mutant helper virus vector comprising the vhs-1 mutation UL41NHB in the virion host shut off gene and an inactivating mutation in the small ribonucleotide reductase (RR) subunit gene; and
   a pharmaceutically acceptable carrier, excipient or diluent,
   wherein expression of the at least one toxic foreign gene inhibits tumor growth upon direct intra-tumor injection of the pharmaceutical composition to the solid tumor.

2. The pharmaceutical composition of claim 1, wherein the solid tumor is a brain tumor.

3. A method for the treatment of an individual having a solid tumor, comprising: administering intra-tumorally by direct injection to the solid tumor in the individual, an HSV1 viral vector comprising an effective amount of a combination of
   an HSV1 amplicon defective viral genome comprising at least one cytotoxic foreign gene selected from the group consisting of thymidine kinase (TK) and/or P53, and
   an HSV mutant helper virus vector comprising the vhs-1 mutation UL41NHB in the virion host shut off gene and an inactivating mutation in the small ribonucleotide reductase (RR) subunit gene,
   wherein expression of the at least one toxic foreign gene inhibits tumor growth.

4. The method according to claim 3, wherein the solid tumor is a brain tumor.

5. A combination pharmaceutical composition for the treatment of a solid tumor in an individual, comprising:
   a first pharmaceutical composition comprising an effective amount of an HSV1 defective viral amplicon genome comprising at least one toxic foreign gene selected from the group consisting of thymidine kinase (TK) and/or P53 and an HSV mutant helper virus vector comprising the vhs-1 mutation UL41NHB in the virion host shut off gene and an inactivating mutation in the small ribonucleotide reductase (RR) subunit gene; and
   a second pharmaceutical composition comprising an effective amount of an HHV-6 or HHV-7 amplicon vector comprising a gene encoding for a peptide capable of enhancing the immune system of a treated individual,
   wherein expression of the at least one toxic foreign gene inhibits tumor growth upon direct intra-tumor injection of the first pharmaceutical composition to the solid tumor, and wherein said peptide capable of enhancing the immune system is IL-2, IL-4, IL-10 or interferon.

6. The combination pharmaceutical composition of claim 5, further comprising a package comprising the first and the second pharmaceutical compositions.

7. A kit, comprising:
   a first pharmaceutical composition comprising an effective amount of an HSV1 defective viral amplicon genome comprising at least one toxic foreign gene selected from the group consisting of thymidine kinase (TK) and/or P53 and an HSV mutant helper virus vector comprising the vhs-1 mutation UL41NHB in the virion host shut off gene and an inactivating mutation in the small ribonucleotide reductase (RR) subunit gene;
   a second pharmaceutical composition comprising an effective amount of an HHV-6 or HHV-7 amplicon vector comprising a gene encoding for a peptide capable of enhancing the immune system of a treated individual; and
   directions for use of the kit,
   wherein expression of the at least one toxic foreign gene inhibits tumor growth upon direct intra-tumor injection of the first pharmaceutical composition to the solid tumor, and wherein said peptide capable of enhancing the immune system is IL-2, IL-4, IL-10 or interferon.

8. The method of claim 3, wherein the HSV1 viral vector is administered to the individual receiving an additional treatment.

9. An injectable composition, comprising:
   a HSV mutant helper virus vector comprising the vhs-1 mutation UL41NHB in the virion host shut off gene and an inactivating mutation in the small ribonucleotide reductase (RR) subunit gene; and
   a pharmaceutically acceptable carrier, excipient or diluent.

10. A method of treating a solid tumor in a subject, comprising:
    administering the injectable composition according to claim 9 to the subject in need thereof, the administering comprising intra-tumoral administration by direct injection.

11. The method according to claim 10, wherein the solid tumor is a brain tumor.

* * * * *